US010582851B2

(12) United States Patent
Donitzky et al.

(10) Patent No.: US 10,582,851 B2
(45) Date of Patent: Mar. 10, 2020

(54) INTEGRATED DEVICE FOR OPHTHALMOLOGY

(71) Applicant: Wavelight GmbH, Erlangen (DE)

(72) Inventors: Christof Donitzky, Eckental (DE); Christian Wuellner, Bräuningshof (DE)

(73) Assignee: Alcon Inc. (CH)

( * ) Notice: Subject to any disclaimer, the term of this patent is extended or adjusted under 35 U.S.C. 154(b) by 0 days.

(21) Appl. No.: 15/725,978

(22) Filed: Oct. 5, 2017

(65) Prior Publication Data

US 2018/0028060 A1 Feb. 1, 2018

Related U.S. Application Data

(63) Continuation of application No. 14/368,782, filed as application No. PCT/EP2011/006614 on Dec. 30, 2011, now abandoned.

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0008* (2013.01); *A61B 3/0091* (2013.01); *A61B 3/107* (2013.01); *A61B 3/1015* (2013.01); *A61B 3/113* (2013.01); *A61B 3/145* (2013.01); *A61B 3/18* (2013.01); *A61B 5/0066* (2013.01); *G02B 27/1013* (2013.01); *G02B 27/141* (2013.01)

(58) Field of Classification Search
CPC ......... A61B 3/102; A61B 3/1015; A61B 3/18; A61B 3/0091; A61B 3/0025; A61B 3/103

USPC ................ 351/246, 206, 220, 212, 211, 221
See application file for complete search history.

(56) References Cited

U.S. PATENT DOCUMENTS 5,914,817 A * 6/1999 Browning .......... G02B 27/1026
359/629
7,815,310 B2 * 10/2010 Su ............................. G01J 9/00
351/205

(Continued)

OTHER PUBLICATIONS

Ibragimov, I.A. "Maximum-Likelihood Method." Encyclopedia of Mathematics, Feb. 7, 2011, www.encyclopediaofmath.org/index.php?title=Maximum-likelihood_method&oldid=13827.*

(Continued)

*Primary Examiner* — Zachary W Wilkes
(74) *Attorney, Agent, or Firm* — Joseph Weatherbee, Esq.

(57) ABSTRACT

A device (100) for ophthalmic radiation is provided. The device comprises a radiation interface (102), an optical branch coupler (104), and a plurality of ophthalmic units (106, 108, 110, 112). The radiation interface is adapted to at least one of output and capture radiation on an optical path (124). The optical path is directable towards a patient's eye. The optical branch coupler is adapted to couple output radiation from a plurality of optical branches (118, 119, 120, 122, 123) into the optical path and to couple captured radiation from the optical path into the optical branches. The captured radiation is spectrally split by the optical branch coupler into the optical branches. Each of the optical branches has a different spectral range. Each of the plurality of ophthalmic units is arranged to couple to one of the optical branches.

3 Claims, 5 Drawing Sheets

(51) Int. Cl.
*A61B 3/14* (2006.01)
*A61B 3/107* (2006.01)
*A61B 3/113* (2006.01)
*G02B 27/10* (2006.01)
*A61B 5/00* (2006.01)
*A61B 3/18* (2006.01)
*G02B 27/14* (2006.01)

(56) References Cited

U.S. PATENT DOCUMENTS

| | | | |
|---|---|---|---|
| 8,693,745 B2* | 4/2014 | Izatt | A61B 3/102 |
| | | | 382/128 |
| 2007/0115552 A1* | 5/2007 | Robinson | G02B 27/1026 |
| | | | 359/487.04 |
| 2007/0252951 A1 | 11/2007 | Hammer et al. | |
| 2009/0009717 A1* | 1/2009 | Barrett | A61B 3/1015 |
| | | | 351/221 |

OTHER PUBLICATIONS

Sakamoto, Julia A., et al. "Inverse Optical Design of the Human Eye Using Likelihood Methods and Wavefront Sensing." Opt. Express, vol. 16, Jan. 7, 2008, pp. 1-17.*

* cited by examiner

INTEGRATED DEVICE FOR OPHTHALMOLOGY

RELATED APPLICATIONS

The present application is a continuation of U.S. patent application Ser. No. 14/368,782 filed Jul. 24, 2014, which is a 371 National Stage application of International Application Serial No. PCT/EP2011/006614 filed Dec. 30, 2011, the disclosures of which are incorporated into the present application.

TECHNICAL FIELD

The present invention generally relates to ophthalmic technology. In particular, the invention relates to an integrated device providing radiation and/or analyzing radiation for ophthalmology.

BACKGROUND

Devices for ophthalmic diagnostics have been designed for very specific diagnostic applications. As an example, the "WaveLight® Topolyzer™ Vario™" and the "WaveLight® Oculyzer™II", each distributed by the applicant, provide topography measurements and Scheimpflug measurements, respectively. Furthermore, some of present-day devices for ophthalmic diagnostics house two different measuring technologies, which can only be applied one after another. The "Visionix L80 Wave+" by Luneau/Visionix is an exemplary device for the latter. Provision and deployment of multiple devices for ophthalmology is disadvantageous because of high floor space requirements and multiple costs for both investment and maintenance, which can even impede an application of ophthalmic devices in medical practises or clinics. Also, cooperation of patients has been observed to cease when the patients undergo multiple measurements using different devices. It would be a significant advance for patients and economically oriented enterprises, including medical practises, clinics and health insurance funds, if it was possible to complete an ophthalmic procedure in shorter time.

SUMMARY

Accordingly, it is an object of the present invention to provide a device for ophthalmology that completes an ophthalmic procedure more rapidly with reduced space requirement.

The object is solved by a device for ophthalmic radiation according to claim 1. The device comprises a radiation interface, an optical branch coupler and a plurality of ophthalmic units. The radiation interface is adapted to at least one of output and capture radiation on an optical path. The optical path is directable towards an eye. The optical branch coupler is adapted to couple output radiation from a plurality of optical branches into the optical path and to couple captured radiation from the optical path into the optical branches. The captured radiation is spectrally split into the optical branches. A different spectral range is coupled into each of the optical branches. Each of the ophthalmic units is arranged to couple to one, two or more of the optical branches.

The radiation interface may have a radiation aperture. The radiation aperture may be realized by an opening in a housing of the device and may include at least one of a translucent window and an entrance lens. The radiation aperture may be adapted to output and/or capture the radiation on the optical path. The coupling of different spectral ranges into the optical branches may relate to the captured radiation from the optical path.

Each of the ophthalmic units can operate in one or more of the different spectral ranges. The operation may include at least one of providing radiation and processing radiation. Each of the ophthalmic units may operate in a spectral range in correspondence to the one or more optical branches the respective ophthalmic units is arranged to couple to. Due to the spectral splitting, the device can provide multiple ophthalmic technologies using one and the same optical path. The spectral splitting may be in accordance with the different spectral ranges. The operation of one or all of the ophthalmic units may include measurements, which may include optical measurements. Some or all measurements may be performed on the optical path, which may define an optical measurement axis. Some or all ophthalmic units may perform their measurements on the optical path and may provide different ophthalmic technologies. The ophthalmic units may be operated independently.

Advantageously in certain embodiments, many steps of one or more ophthalmic procedures can be completed in a shorter time. Using the same optical path, a more compact design of the device is achievable. Furthermore, the device can provide to a patient a uniform interface for a plurality of different ophthalmic technologies. A single uniform interface may be achieved by virtue of the radiation interface. Usage of several devices can be avoided. The device can complete ophthalmic procedures more rapidly. More patients can receive the latest ophthalmic technology faster and at lower costs.

In particular, the device may be a device for optical ophthalmic or ophthalmologic analysis, diagnostics, and/or treatment. The analysis, diagnostics, or treatment may be contactless. The optical path may be the sole optical path of the device directable towards the eye. The coupling of the output radiation from the plurality of optical branches into the optical path may be a composition of the output radiation. The coupling of the captured radiation from the optical path into the optical branches may be a decomposition of the captured radiation. Throughout, the terms "light" or "optical", or the prefix "photo-" can refer to electromagnetic radiation, or a component processing the same, in at least one of the infrared spectrum, the visual spectrum and the ultraviolet spectrum. Each of the spectral ranges in which a respective one of the ophthalmic units operates may be useful for a particular measurement. The operation of an ophthalmic unit can include at least one of analysis of captured radiation and emission of output radiation.

The different spectral ranges may have at least one of different wavelengths (or frequencies) of electromagnetic radiation, different spectral maxima, different spectral centers, non-overlapping spectral ranges, separate spectral ranges, and disjoined spectral ranges. Based on the spectral splitting into the different spectral ranges, at least those ophthalmic units that are operable at the different spectral ranges may be independently designed. The ophthalmic units may be specified to operate within a predefined spectral range and may operate exclusively in that predefined spectral range. The predefined spectral range may be a subset of the different spectral ranges. As an advantage, the development of the device or a further development of the ophthalmic units may be distributed.

Alternatively or in addition, the ophthalmic units or their operation may be interdependent. By example, a first ophthalmic unit can comprise an excitation light source adapted to emit excitation light in a first spectral range into a first optical branch. The captured radiation may comprise in a second spectral range fluorescent light. The fluorescent light may be induced, e.g., due to a fluorescent dye applied to the eye, by the excitation light. A second ophthalmic unit may be adapted to detect the fluorescent light. The second ophthalmic unit may be coupled to a second optical branch corresponding to the second spectral range. Alternatively, the second ophthalmic unit may also be coupled to the first optical branch. The first optical branch may carry radiation in both the first spectral range and the second spectral range.

The optical coupler may include one or more beam splitters. Each of the one or more beam splitters may have a different spectral transmittance and/or a different spectral reflectance. Generally, the splitting may be based on interference in a coating, a layer, or a thin film. Each of the one or more beam splitters may comprise one or more of a pair of triangular glass prisms glued to each other, a partially transmissive mirror, a plate of glass with a thin coating providing partial reflection, a dichroic mirror, a substrate with a thin dielectric layer, a series of such layers, a series of an alternating arrangement of a metallic layer and a dielectric layer, and a dichroic prism. The triangular glass prisms may include isosceles and right-angled triangular glass prisms. The triangular glass prisms may be pairwise glued and may be glued to each other at the base surface.

The optical coupler may include a dichroic prism. The dichroic prism may be multibranched (also referred to as a "multichannel dichroic prism"). Generally, the spectral splitting can be based on dichroism, particularly by means of interference and/or birefringence. The multibranched dichroic prism may comprise two or more glass prisms that have optical interfaces that include optical coatings adapted to selectively transmit or reflect radiation depending on the wavelength of the radiation, e.g., by means of interference, as mentioned above. Alternatively or in addition, the multibranched dichroic prism may comprise one or more of a dichroic crystal as a monocrystal and a birefringent crystal as a monocrystal. The multibranched dichroic prism may comprise one or more prisms made of a dichroic crystal or a birefringent crystal. A prism including at least one of a dichroic crystal and a birefringent crystal is collective referred to as "crystal prism". The crystal or the crystal prism may have an index of refraction depending on at least one of the wavelength of the radiation and the polarization of the radiation. The dichroic splitting of the radiation can be much more efficient as compared to subtractive filters. Thus, an intensity of the output radiation applied to the eye, e.g. for illumination, can be reduced. Alternatively or in addition, the crystal or the crystal prism may have an absorptance depending on at least one of the wavelength of the radiation and the polarization of the radiation.

The optical interfaces of the prisms, e.g., the glass prisms and/or the dichroic crystal prisms, may be arranged in direct contact and/or glued together. This allows for an even more compact design of the optical branch coupler, and thus of the device. Furthermore, the device is more robust. The device may be more shockproof due to the defined relative arrangement of optical components. The arrangement might be advantageous, e.g., when the device is a mobile device or a table-top device.

The ophthalmic units may be operated simultaneously. The operation of any of the ophthalmic units may include at least one of analysis of the captured radiation and emission of the output radiation. As a result, several steps of the procedure may be performed in parallel. Thus, the time required for ophthalmic diagnostics and/or ophthalmic treatment can be reduced.

A total number of the optical branches in the device may be two, three, four or five. The number of optical branches can correspond to the number of ophthalmic units coupled to one of the optical branches. This allows for including a plurality of ophthalmic units and corresponding ophthalmic technologies without increasing the size and complexity of the optical path or the radiation interface as the output of the device. Also, output optics may be shared by some or all ophthalmic units. The output optics may be arranged in the optical path.

Moreover, two or more of the ophthalmic units may be arranged to couple to one of the optical branches. Thus, optical elements may be shared. For example, those optical elements that are used for two or more ophthalmic units may be shared. As a result, the two or more ophthalmic units can be reduced in size for a still more compact design of the device.

The optical branch coupler may be arranged on the optical path. The optical branches may have a star-shaped arrangement with respect to the optical branch coupler. Similarly, the corresponding ophthalmic units coupled to the optical branches may have a star-shaped arrangement. The optical lengths of the optical branches may be adjustable or fixed. The optical lengths of the optical branches may be equalized or balanced. The optical branch coupler may be arranged, e.g., centered, in between the ophthalmic units. The ophthalmic units can be distributed in two dimensions or three dimensions with respect to the optical branch coupler. In the case of three optical branches, the optical path and the three optical branches may be arranged in a tetrapod structure. In the tetrapod structure, the optical path and the three optical branches, or their linear extensions, may enclose a tetrahedral angle. In the case of three ophthalmic units, the ophthalmic units may be arranged at three of the four tetrahedron vertices. The optical branch coupler may be located at the center of the tetrahedron.

The radiation interface may be any at least partially transparent surface or an opening. The radiation interface can include output optics, particularly an objective. In certain embodiments, optical elements used, e.g., for directing the optical path towards the eye, by two or more of the plurality of ophthalmic units may be arranged as one interface towards the eye on the optical path. This allows the number of optical elements and the size of the device to be reduced.

One or more of the ophthalmic units may be adapted to insert output radiation into its optical branch for ophthalmic treatment. The inserted output radiation can be laser light for ablation or ultraviolet light for cross-linking. The cross-linking (also referred to as "curing" or "hardening") may include a photooxidative cross-linking. UV-A light may be used for the cross-linking in conjunction with riboflavin, organic molecules in the class of diazirines, or any other suitable crosslinker. Alternatively or in addition, the device may perform a refractive surgery of the eye or a treatment of keratoconus. The output radiation may be in the UV, visible, or IR spectrum. The output radiation may be generated by an ultrashort pulse laser, such as a femtosecond laser or a picosecond laser or an attosecond laser. Advantageously, a result of the surgery or treatment can be observed or quantified in real time by one or more of the other ophthalmic units.

One of the ophthalmic units may comprise a fixation unit adapted to at least one of detect a position of the eye, detect a movement of the eye, provide a fixation target, and/or provide an accommodation target on which the patient may focus. The eye may be detected by image recognition of pupil or iris. A measurement can be corrected or discarded depending on a position or a movement of the eye detected by the fixation unit. The measurement may be performed simultaneously by one or more of the other ophthalmic units. The position of the eye or the movement of the eye can be controllable by the fixation target or a virtual image thereof. The fixation target or its virtual image may be moveable. An accommodation state of the eye may be controllable by the accommodation target or a virtual image thereof. The accommodation target or its virtual image can be shiftable in focal length.

The optical branch of the fixation unit, i.e., the optical branch coupled to the fixation unit, may pass straight through the optical branch coupler. Alternatively, the ophthalmic unit inserting output radiation for ophthalmic treatment may be arranged on a straight line extending the optical path. In both cases, the other optical branches may extend laterally to the optical path. Accordingly, the number of reflections on the optical branch passing straight through the optical branch coupler can be minimized. Minimizing the number of reflections may be advantageous for analyzing captured radiation of low intensity or emitting output radiation of high intensity. "Low" may relate to 5% or less, e.g., 1%, of an cornea illumination intensity. "High" may relate to 50% or more of a cornea ablation intensity or disruption intensity.

One of the ophthalmic units may be an Optical Coherence Tomography (OCT) unit. The OCT unit may be adapted to perform an OCT measurement. The OCT unit may comprise a low-coherence light source (e.g., a Light Emitting Diode (LED), a broadband light source, a Supercontinuum Light Source, Swept source, e.g. for Time Encoded Frequency Domain OCT, a Ti: Sapphire laser, or a Superluminescent Diode (SLD)) and an interferometer. As a result, a map of cornea thickness can be determined, e.g., by means of Optical Low-Coherence Reflectometry (OLCR), which is also referred to as Optical Coherence Pachymetry (OCP) in this context.

Optical lengths of the optical branches in the multi-branched dichroic prism may be different. The different optical lengths of the respective optical branches may correspond to different penetration depths or measurements layers of the OCT measurement. Based on two different optical lengths of two respective optical branches, spatially separated sections are simultaneously detectable, such as spatially separated anatomies or tissues, particularly the anterior segment and the posterior segment of the eye, e.g., two or more of cornea, lens, retina, and other anatomies.

One or more of the ophthalmic units may be a wavefront unit adapted to measure a wavefront of the capture radiation. The wavefront unit may comprise a wavefront light source and a lenslet array. For example, the wavefront unit and the OCT unit may share a broadband light source. Consequently, the OCT unit and the wavefront unit may be reduced in size, thus allowing for a still more compact design of the device. The wavefront unit may further comprise a narrowband filter, which may be applied to the light source when the wavefront unit is operated.

The retina and/or the macula of an eye may be inspected using OCT. Alternatively or in addition, the retina and/or the macula of the eye may be detected using OCT for determining an optical length or physical length of an axis of the eye or for detecting an Age-related Macular Degeneration (AMD). Alternatively or in addition, the retina and/or the macula of the eye may be traced for the aforementioned fixation of the eye.

Alternatively or in addition, one or more of the ophthalmic units may be a Scheimpflug unit adapted to perform a Scheimpflug measurement. The Scheimpflug measurement may provide at least one of values of height of an anterior chamber of the eye, a map of refractive power, a posterior corneal shape, and corneal thickness. The lens, i.e. a contour and/or a shape of the lens, of an eye may be measured using OCT. The shape of the lens may be an optically effective shape.

One or more of the ophthalmic units may be a corneal topography unit adapted to measure a topography of a cornea surface, particularly an anterior cornea surface, of the eye. Alternatively or in addition, one or more of the ophthalmic units may be a keratometer unit adapted to determine a curvature of a cornea surface, particularly an anterior cornea surface, of the eye.

Moreover, one or more of the ophthalmic units may be an illumination unit adapted to generate radiation for a slit illumination of the eye. At least one of the corneal topography unit, the keratometer unit and the illumination unit may comprise a projector adapted to generate output radiation projecting an intensity pattern. Two or more of the Scheimpflug unit, the corneal topography unit, the keratometer unit and the illumination unit may share one projector. The projector may comprise a microdisplay or a micromirror array.

The device may further comprise a controller adapted to control each of the plurality of ophthalmic units. The projector may be adapted to project the intensity pattern in response to a digital image signal provided by the controller. The controller may be further adapted to compute optimized values based on results determined by two or more of the ophthalmic units. The optimization may include computing an average of the results or a maximum likelihood computation of the results. The results of the different ophthalmic units may be weighted according to accuracy or precision. The accuracy or precision may be determined by the ophthalmic units and/or the individual results. The different ophthalmic units may apply different ophthalmic technologies.

BRIEF DESCRIPTION OF THE DRAWINGS

For the purpose of illustration and not limitation, further aspects, advantages and features of the technique presented herein will become apparent from the following description of exemplary embodiments and the drawings, wherein.

DETAILED DESCRIPTION

Figure 1:
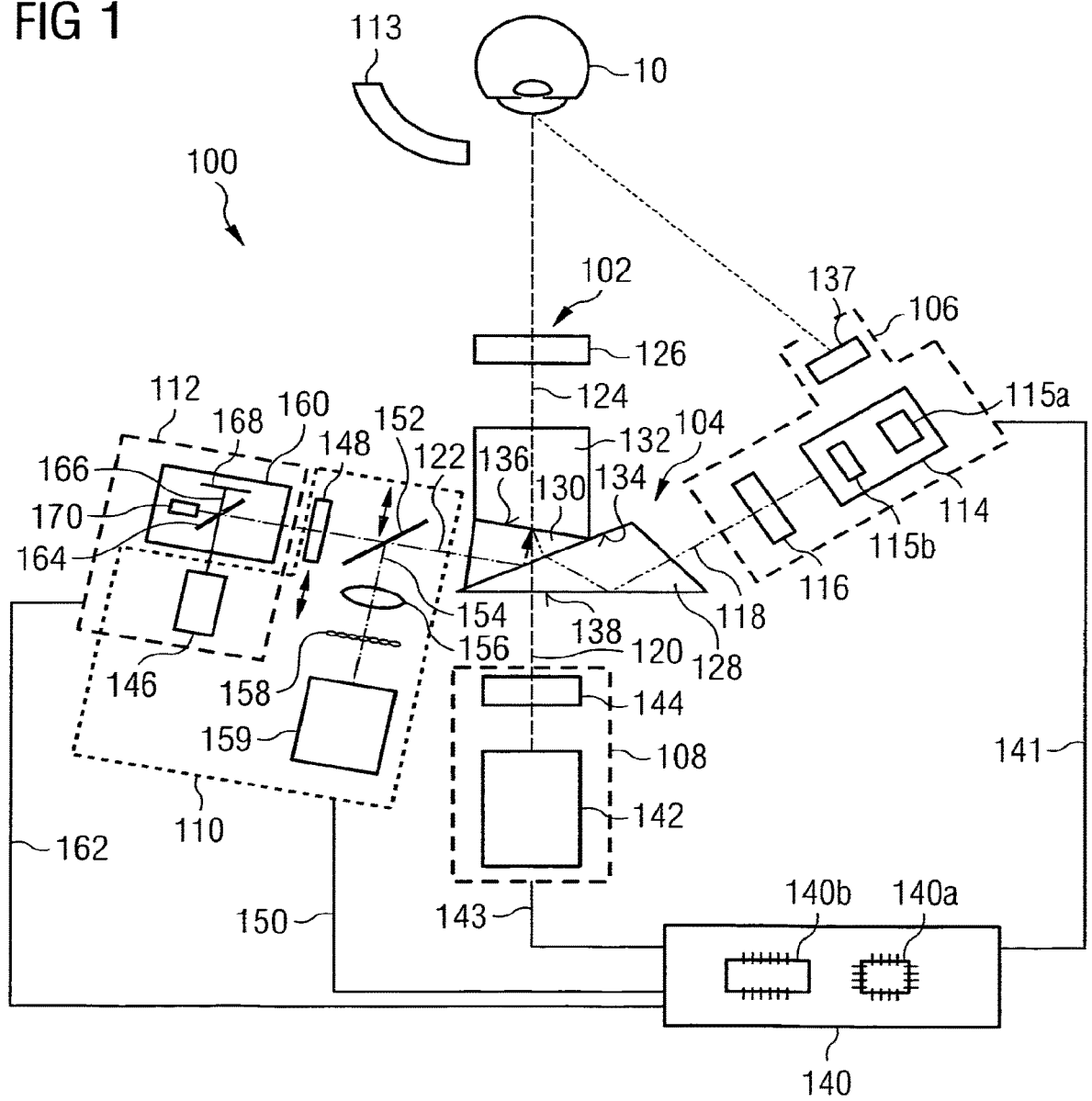
FIG. 1 schematically illustrates a first embodiment of a device for ophthalmic radiation.

FIG. 1 schematically shows a functional arrangement of optical components in a device 100 for ophthalmic radiation. Throughout, like reference signs indicate equivalent or alternative features or components. The device 100 comprises a radiation interface 102 (e.g., a radiation outlet), an optical branch coupler 104, and a plurality of ophthalmic units 106, 108, 110 and 112. The device comprises a supporting surface or a contact surface 113 for a patient's head. The supporting surfaces or contact surfaces define a position of an eye 10 relative to the device 100 or to the radiation interface 102.

The ophthalmic unit 106, in the embodiment shown in FIG. 1, is an illumination unit comprising a projector 114 for a slit lamp illumination at the eye. The projector 114 includes a light source 115a, e.g., one or more LEDs, and a microdisplay 115b. The microdisplay 115b can comprise a silicon chip as a substrate material and addressing electronics of an active matrix with integrated drivers on the substrate material. The light source can provide a background illumination for liquid crystals on the silicon chip, which may be controlled by electrodes on the silicon chip. Alternatively, the silicon chip can support a matrix of tiltable mirrors, also referred to as a Digital Micromirror Device (DMD) or Digital Light Processing (DLP) device. A shape of controllable segments on the silicon chip can include at least one of a set of concentric rings (also referred to as "Placido rings"), a set of parallel stripes (which may be selectively activated for the slit lamp illumination) and a matrix of pixels. In response to a digital image signal, the matrix of pixels selectively generates the set of rings, the set of parallel stripes or a light intensity pattern defined by the digital image signal. The illumination unit 106 further comprises optics 116 adapted to project the light intensity pattern into a first optical branch 118 of the optical branch coupler 104. A focal length of the optics 116 is variable. The focal length can be manually set or automatically adjusted to a surface of the eye 10. The optics 116 can further include one or more of a filter, a collimator, a polarizer, and a phase plate.

The optical branch coupler 104, shown in the embodiment of FIG. 1, provides three branches (or channels). The first optical branch 118 is coupled to the illumination unit 106. A second optical branch 120 is coupled to the ophthalmic unit 108, which is or includes a fixation unit in the embodiment shown in FIG. 1. A third optical branch 122 is coupled to both the ophthalmic unit 110 and the ophthalmic unit 112. In the embodiment shown in FIG. 1, the ophthalmic unit 110 is a wavefront unit and the ophthalmic unit 112 is an Optical Coherence Tomography unit, or OCT unit.

As is explained below in more detail with reference to FIGS. 4 to 6, the optical branch coupler 104 is adapted to receive radiation from each of the optical branches 118, 120 and 122. Each of the optical branches 118, 120 and 122 has a specific spectral range. The radiation of the optical branches 118, 120 and 122 is composed by the optical branch coupler 104 into a single optical path 124. The composed radiation is output on the optical path 124 at the radiation interface 102 directed towards the eye 10.

In the embodiment shown in FIG. 1, the radiation interface 102 comprises interface optics 126 arranged on the optical path 124. In the direction of output radiation, the optics 126 is arranged behind the optical branch coupler 104.

The interface optics 126 is adapted to collect or capture radiation (such as light emitted or reemitted from the eye 10) on the optical path 124.

The captured radiation enters the optical branch coupler 104, which spectrally splits the captured radiation according to the specific spectral ranges into a corresponding one of the optical branches 118, 120 and 122. In the embodiment shown in FIG. 1, the optical branch coupler is a multibranched dichroic prism comprising three dichroic prisms 128, 130 and 132. The dichroic prisms 128, 130 and 132 are glued pairwise at optical interfaces 134 and 136, respectively. The multibranched dichroic prism thus forms an integral optical branch coupler 104. The captured radiation on the optical path 124 passes through the dichroic prism 132 and is split into two intermediate branches at the optical interface 136 in the dichroic prism 130. One of the two intermediate branches is partially reflected at the optical interface 134 between the dichroic prisms 128 and 130. The reflected portion of the intermediate branch defines the third optical branch 122. A transmitted portion of the one intermediate branch passes through the prism 128 and defines the second optical branch 120. The other of the two intermediate branches passes through the optical interface 134 and is reflected (due to total internal reflection) at a bottom surface 138 of the dichroic 128. The totally reflected intermediate branch defines the first optical branch 118.

The splitting of the optical path 124 into the two intermediate branches depends on the wavelength of the radiation. Consequently, the optical interface 136 provides a first spectral splitting. The partial reflection and partial transmission at the optical interface 134 also depends on the wavelength of the radiation. Consequently, the partial reflection and partial transmission is a further spectral sub-splitting. As a result, the captured radiation entering the optical branch coupler 104 on the optical path 124 (through the radiation interface 102) is spectrally decomposed into the three optical branches 118, 120 and 122.

The ophthalmic units 106, 108, 110 and 112, each of which being coupled to one of the optical branches 118, 120 and 122, at least one of analyses the captured radiation in the specific spectral range of the corresponding optical branch and emits into the corresponding optical branch output radiation in the specific spectral range of the respective optical branch. In the embodiment shown in FIG. 1, the illumination unit 106 emits light at a wavelength of, e.g., 475 nm. The fixation unit 108 emits light at a wavelength of, e.g., 532 nm. The wavefront unit 110 emits radiation at, e.g., 810 nm. The OCT unit 112 emits broadband radiation in the spectral range of, e.g., 760 nm to 860 nm or to 960 nm. The optical branch coupler 104 is adapted to split the captured radiation on the optical path 124 into the first optical branch 118 including a spectral range up to, e.g., 500 nm (with a short-wavelength cut-off, e.g., at about 390 nm), into the second optical branch 120 in a spectral range of, e.g., 500 nm to 750 nm, and into the third optical branch 122 including a spectral range above, e.g., 750 nm (with a long-wavelength cut-off, e.g., at about 900 nm, 960 nm or 1000 nm).

The device 100 further comprises a controller 140 electrically connected to each of the ophthalmic units 106, 108, 110 and 112 via signal lines 141, 143, 150, 162, respectively. The controller 140 comprises a central processing unit (CPU) 140a and a graphics engine 140b. The graphics engine 140b generates the digital image signal on the illumination signal line 141 to the illumination unit 106. The projector 114 of the illumination unit 106 generates a two-dimensional intensity pattern of light corresponding to the digital image signal. The digital image is projected by the projection optics 116 in the first optical branch 118 and thus by means of the optical branch coupler 104 in the optical path 124. A focal length of the projection optics 116 is adjusted to project the digital image onto a surface of the eye 10. The illumination unit 106 thus provides the functionality of a digital slit lamp. The controller 140 allows a user to shift a position of a slit illumination on the eye 10 and to rotate the slit illumination by 360°.

In an extended embodiment (not shown), the illumination unit 106 further comprises a digital camera (not shown) adapted to capture the radiation reflected from the eye in the spectral range of the projector 114. In a variant of the embodiment, two or three cameras are provided for triangulation. The controller 140 is adapted to control the projector to project Placido rings or a grid pattern onto the eye 10, particularly onto an anterior surface of the cornea of the eye. The controller 140 is further adapted to analyze the digital image captured by the digital camera and to determine several thousand height values or curvature values of the anterior surface of the cornea. The illumination unit 106 in the extended embodiment thus provides the functionality of a corneal topographer (also referred to as a "video keratograph").

Still further, the controller 140 is adapted to vary the size of the digital image projected by the illumination unit 106 onto the eye 10. The (same) image is projected onto the cornea at different sizes. The camera captures reflections and/or backscattering of the image projected onto the cornea at different sizes. The CPU 140a of the controller 140 is adapted to compute, using a general lens formula, the curvature of the anterior surface of the cornea based on the captured reflections and/or backscattering. The illumination unit 106 thus also provides the functionality of a keratometer or ophthalmometer.

The fixation unit 108 comprises a fixation light source 142 providing a fixation target to a patient. The fixation unit optionally comprises an accommodation optics 144. The focal length and/or astigmatic compensation of the accommodation optics is variable and controlled by the controller 140. Thus, the device 100 can provide (as a single image) both a fixation target and an accommodation target to control the fixation or the orientation of the eye 10 and the accommodation of the eye 10, respectively.

The wavefront unit 110 comprises a broadband light source 146. In the embodiment shown in FIG. 1, the broadband light source 146 is a superluminescent diode (SLD), or any other suitable broadband light source, covering a spectrum of 810±100 nm. Alternative center wavelengths include 800 nm and 840 nm (at the bandwidth of ±100 nm). The wavefront unit 110 further comprises a narrowband filter 148. A spectral transmittance of the narrowband filter 148 has a sharp peak at the center wavelength (which is 810 nm in the embodiment shown in FIG. 1). The bandwidth of the narrowband filter 148 is characterized by a Full Width at Half Maximum (FWHM) of 10 nm or less, e.g., of 5 nm. The narrowband filter 148 is pivotable between a disabled position outside the third optical branch 122 and an enabled position, in which the narrowband filter 148 is centered on the third optical branch 122. In an exemplary embodiment, an actuator is adapted to induce the pivoting movement of the narrowband filter 148. The actuator pivots the narrowband filter 148 in the enabling position in response to an enabling signal on the wavefront signal line 150 provided by the controller 140. The wavefront unit 110 further comprises a partially transmissive mirror 152 pivotable between a disabling position fully outside the third optical branch 122 and an enabling position. In the enabling position of the mirror 152, an active surface of the mirror 152 is arranged at an angle of incidence of approximately 45° with respect to the third optical branch 122. In an exemplary embodiment, an actuator provides the pivoting movement of the mirror 152. The actuator for the movement of the narrowband filter 148 and the actuator for the movement of the mirror 152 are electrically coupled for a synchronous movement of both the narrowband filter 148 and the mirror 152. Alternatively, the actuator of the narrowband filter 148 and the actuator of the mirror 152 is one actuator, wherein the movement of the narrowband filter 148 and the mirror 152 is mechanically coupled or optically arranged.

The light source 146 and the narrowband filter 148 generate, in response to the enabling signal on the wavefront signal line 150, light at the central wavelength as output radiation on the third optical branch 122. The output radiation at least partially passes through the partially transmissive mirror 152, is combined or combinable with output radiation on the other optical branches 118 and 120 by the optical branch coupler 104, and is output at the radiation interface 102 on the optical path 124. The output radiation of the wavefront unit 110 is adapted to create a virtual light source in the retina of the eye 10.

The output radiation of the wavefront unit 110 thus induces secondary radiation coming out of the eye 10. The device 100 at least partially captures the secondary radiation on the optical path 124. The captured radiation induced by the wavefront unit 110 has essentially the same wavelength of the output radiation of the wavefront unit 110. Consequently, the optical branch coupler 104 directs the captured radiation induced by the output radiation of the wavefront unit 110 into the third optical branch 122. The partially transmissive mirror 152 partially reflects the captured radiation into a side branch 154. The wavefront unit further comprises a collimator 156, e.g., a single collimating lens. The collimator 156 is adapted to collimate ideal captured radiation of an ideal virtual light source. More specifically, the collimator is adapted to image a captured wavefront (i.e., a spherical wavefront or a wavefront of an ideal point source) to a plane wavefront. In a reduced embodiment, the collimator 156 is omitted.

The wavefront unit 110 further comprises a lenslet array 158 and an image sensor 159. The collimator 156, the lenslet array 158 and the image sensor 159 are arranged on the side branch 154 in sequential order. Each lenslet in the lenslet array 158 is a focussing lens. The lenslets in the lenslet array 158 have a common focal plane. The image sensor 159 is arranged in the common focal plane. While ideal captured radiation from an ideal virtual light source would generate an ideal spot diagram on the image sensor 159, deviations from the ideal spot diagram correspond to the deviations of the wavefront of the captured radiation. More specifically, a lateral shift of a spot in the spot diagram (with respect to the ideal spot diagram) corresponds to a local tilt or variations of the wavefront of the captured radiation. A digital image signal from the image sensor 159 is transmitted on the wavefront signal line 150 to the controller 140. The controller 140 is further adapted to derive a refractive power of the eye 10 based on the digital image signal from the image sensor 159. The wavefront unit 110 (when controlled by the controller 140) provides a wavefront measurement of the eye 10. The wavefront unit 110 is also referred to as an aberrometer unit. Based on the digital image signal from the image sensor 159, the controller 140 is further adapted to determine as components of corrections a sphere component (in the case of farsightedness or nearsightedness), a cylinder component (in the case of astigmatism) and/or an axial component (of the cylinder component).

The OCT unit 112 comprises the broadband light source 146 and an interferometer 160. The OCT unit is enabled in response to an OCT enabling signal on the OCT signal line 162 from the controller 140. Prior to transmitting the OCT enabling signal on the OCT signal line 162, the controller 140 transmits the disabling signal on the wavefront signal line 150. The broadband light source 146 thus emits radiation with a bandwidth of Full Width at Half Maximum (FWHM) equal to or greater than 100 nm. The output radiation on the third optical branch 122 thus has low temporal coherence (corresponding to a coherence length of few μm).

The interferometer 160 comprises a partially transmissive mirror 164, a reference branch 166, and a reference mirror 168 arranged on and perpendicular to the reference branch 166. The interferometer 160 further comprises a photo sensor 170. In the embodiment shown in FIG. 1, the reference branch 166 is on a straight line extending a light beam generated by the broadband light source 146. The photo sensor 170 is arranged on a straight line extending the third optical branch 122 (in continuation through the partially transmissive mirror 164). A reference actuator (not shown) is mechanically coupled to the reference mirror 168. The reference actuator is adapted to adjust an optical length of the reference branch 166. The optical length of the reference branch 166 defines an OCT measurement depth in the eye 10. The output radiation of the OCT unit 112 on the third optical branch 122 is output via the optical branch coupler 104 at the radiation interface 102. The output radiation of the OCT unit 112 induces a reflection radiation or a scattering radiation from the eye 10. The reflection radiation or scattering radiation is at least partially captured through the radiation interface 102. The optical branch coupler 104 directs a captured radiation component on the optical path 124 of the reflection radiation or scattering radiation into the third optical branch 122. The captured radiation that passes through the partially transmissive mirror 164 and reference radiation from the reference branch 166 that is reflected by the partially transmissive mirror 164 is detected by the photo sensor 170. The photo sensor 170 generates an interference signal indicative of an interference of the captured radiation and the reference radiation. The photo sensor 170 transmits the interference signal on the OCT signal line 162 to the controller 140. The controller 140 is electrically coupled to the reference actuator via the OCT signal line 162. The controller 140 is adapted to control the reference actuator so as to adjust the optical length of the reference branch 166. The controller 140 is further adapted to analyze the interference signal from the photo sensor 170. The controller 140 derives one or more OCT measurement values based on the interference signal indicative of, e.g., cornea thickness, anterior chamber depth, lens position, lens thickness, axial length of the eye, and retina thickness.

The OCT unit 112 further comprises a XY-scanner adapted to direct the output radiation of the OCT unit 112 to a plurality of locations on the eye 10 by means of reflection or transmission. The XY-scanner is controlled via the OCT signal line 162 by the controller 140. The controller 140 is further adapted to derive a map of OCT measurement values corresponding to each of the plurality of locations. In an extended embodiment of the device 100, the controller 140 is further adapted to generate a three-dimensional image of an anterior segment and/or a posterior segment of the eye 10. The controller 140 can thus provide to a user a real time image of segments of the eye 10 concurrent to an operation of one or more of the other of ophthalmic units 106 and 108. In deriving the OCT measurement values or providing a three-dimensional image thereof, the controller 140 applies a mathematical correction by ray tracing in order to determine physical lengths.

In a still further embodiment of the device 100, the OCT unit 112 is adapted to generate output radiation comprising a first polarisation state (which may be linear) and an orthogonal second polarisation state (which may be linear). The OCT unit 112 comprises a birefringent crystal (not shown) arranged on the third optical branch 122 and having an extraordinary axis (or "optic axis") perpendicular to the optical branch 122. The first polarisation state is parallel to the extraordinary axis. Both of the output radiation and the captured radiation pass through the birefringent crystal (in the opposite direction, respectively). The passage through the birefringent crystal has different optical lengths for the first polarisation state and the second polarisation state, respectively. The difference of the optical lengths corresponds to twice the difference of optical lengths for a single pass through the birefringent crystal of length L, or $2\cdot(n1-n2)\cdot L$, wherein n1 and n2 denote the index of refraction for the first and the second polarisation state, respectively. The photo sensor 170 is adapted to substantially simultaneously detect the interference signal for each of the first and the second polarisation state. Based on the interference signals for the first and the second polarisation state, different the OCT measurement can substantially simultaneously cover two OCT measurement depths.

Anyone of the embodiments of the device 100 is extendable, wherein the illumination unit 106 is further adapted to perform a Scheimpflug measurement. To this end, the ophthalmic unit 106 further comprises a Scheimpflug camera 137 arranged in a Scheimpflug position. The controller 140 generates a digital image signal on the illumination signal line 141 corresponding to a rotating slit illumination of the eye 10. The controller 140 is further adapted to analyze a digital image signal received on the illumination signal line 141 from the Scheimpflug camera 137. The analysis includes a mathematical correction determining physical lengths based on ray tracing. The ray tracing corrects, based on variations in the refractive index in the eye 10, for a difference in optical length and physical length as well as for a deviation from straight-line propagation. The controller 140 is adapted to derive values of height of the anterior chamber of the eye 10 based on the digital image signal of the Scheimpflug camera 137. Additionally, the controller 140 is adapted to compute a map of refractive power of the eye 10.

Figure 2:
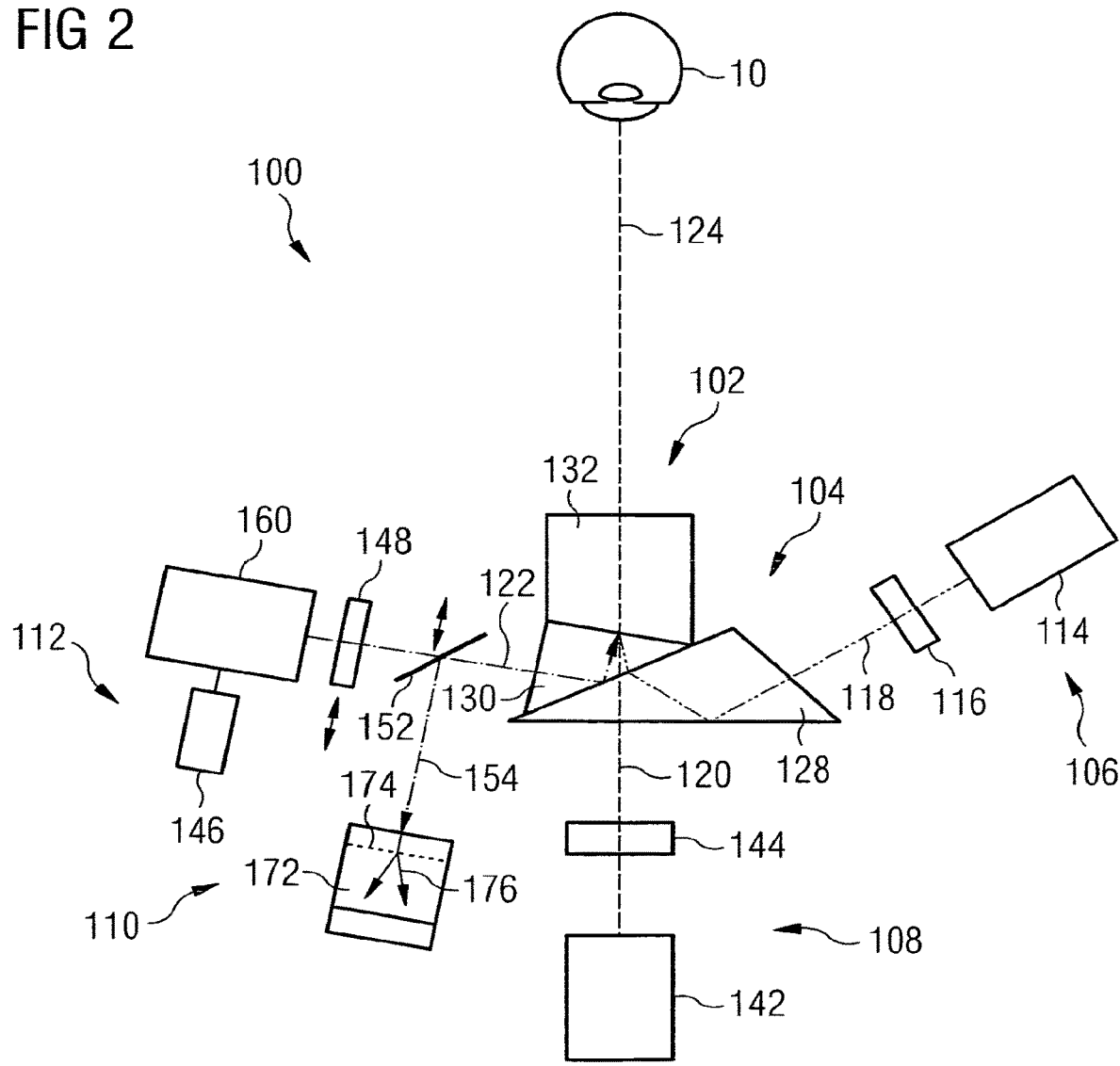
FIG. 2 schematically illustrates a second embodiment of a device for ophthalmic radiation.

A second embodiment of the device 100 is shown in FIG. 2. The device 100 according to the second embodiment differs from the first embodiment in that the radiation interface 102 is an output surface of the optical branch coupler 104 (without the interface optics 126 shown in FIG. 1). The device 100 also comprises an illumination unit 106, a fixation unit 108, a wavefront unit 110 and an OCT unit 112. The wavefront unit 110 comprises a digital wavefront sensor 172 (as an alternative to the lenslet array 158 and the image sensor 159). The digital wavefront sensor 172 comprises a two-dimensional diffraction grating or lattice 174 adapted to replicate (e.g., by means of diffraction) the captured radiation on the side branch 154 into four beams 176. The beams 176 are essentially identical with respect to their wavefront. Each of the beams 176 propagates along a laterally offset direction (i.e., at a small angle with respect to the propagation direction of the side branch 154). The propagation direction of the four offset beams 176 is offset in a vertical plane perpendicular to the side branch 154 in a bottom-left direction, a bottom-right direction, a top-left direction and a top-right direction (two of which are shown in FIG. 2). The detector 172 is adapted to detect an interference signal of the differently offset beams 176 originating from neighbouring positions at the grating or lattice 174. The interference signal indicates a relative phase difference, a local tilt or local variations of the wavefront.

Figure 3:
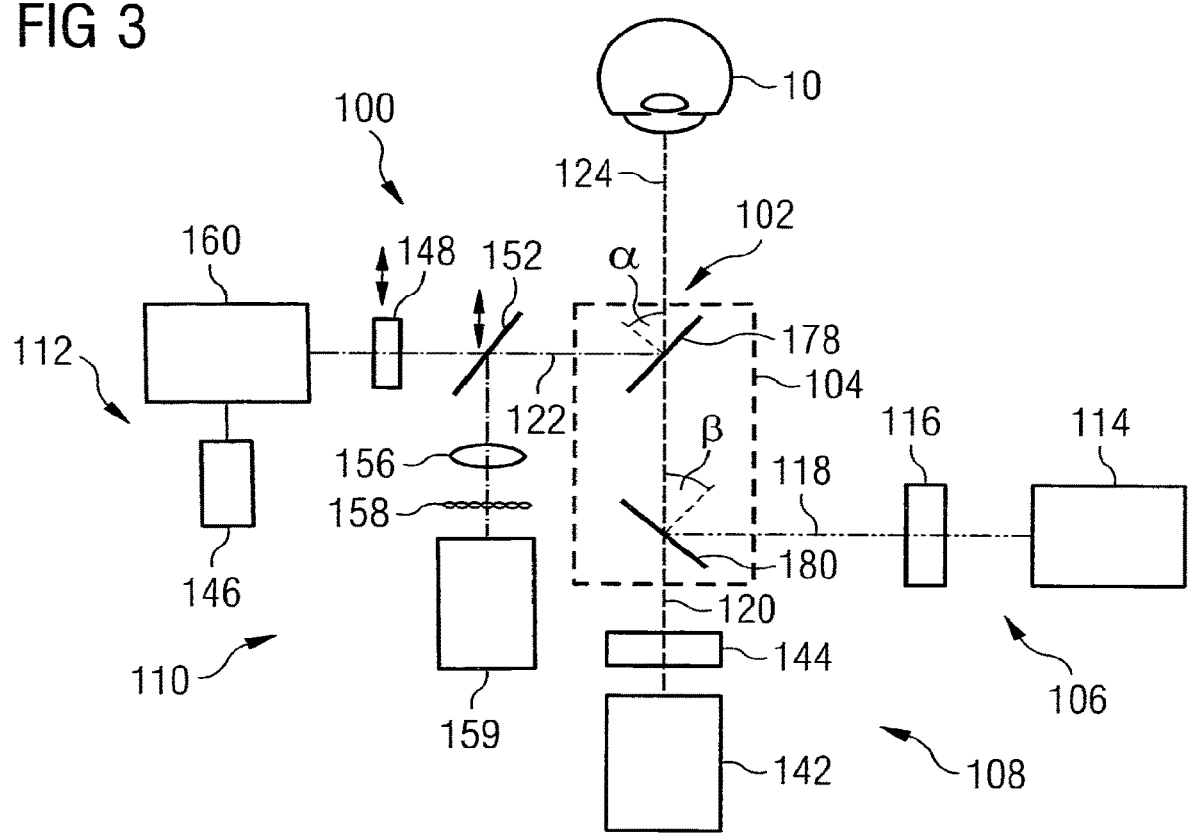
FIG. 3 schematically illustrates a third embodiment of a device for ophthalmic radiation.

FIG. 3 schematically shows a third embodiment of the device 100 for ophthalmic radiation. The device 100 comprises a radiation interface 102 defining an optical path 124, an optical branch coupler 104 and a plurality of ophthalmic units 106, 108, 110 and 112. Each of the ophthalmic units can correspond to the ophthalmic units described above with reference to the first embodiment or the second embodiment.

The optical branch coupler 104 according to the third embodiment shown in FIG. 3 differs from the branch couplers 104 as described above. The optical branch coupler, according to the third embodiment, comprises a first partially transmissive mirror 178 and a second partially transmissive mirror 180. The first partially transmissive mirror 178 comprises a planar glass plate covered by a first partially transmissive layer. A transmittance $T_1$ ($\lambda$) of the first partially transmissive mirror 178 or the first partially transmissive layer depends on the wavelength $\lambda$ of the output or captured radiation. The first transmittance $T_1$ is essentially 100% for wavelengths $\lambda$ below 750 nm. In general, essentially equal to 100% means above 90%, e.g., above 95%. The first transmittance $T_1$ sharply drops at about 750 nm. For example, the first transmittance $T_1$ drops from above 90% to below 10% in a spectral range from 710 nm to 790 nm. The first transmittance $T_1$ is essentially 0% at wavelength 2 above 790 nm. In general, essentially equal to 0% means below 10%, e.g., below 5%.

The second partially transmissive mirror 180 comprises a planar glass plate covered by a second partially transmissive layer. A second transmittance $T_2$ ($\lambda$) of the second partially transmissive mirror 180 or the second partially transmissive layer depends on the wavelength $\lambda$ of the output or captured radiation. The second transmittance $T_2$ is essentially equal to 0% at wavelengths below 500 nm. The second transmittance $T_2$ steeply increases at about 500 nm. The second transmittance $T_2$ is essentially equal to 100% for wavelengths above 500 nm. The second transmittance $T_2$ increases from below 10% to above 90% in a spectral range from 450 nm to 550 nm. An absorptance of both the first and the second partially transmissive mirror 178, 180 is neglectable or below 2%, e.g., below 1%.

The first partially transmissive mirror 178 is arranged on the optical path 124. At the first partially transmissive mirror 178, the optical path 124 encloses an angle of incidence $\alpha$ to the normal of the first partially transmissive mirror 178. The second partially transmissive mirror 180 is arranged on the optical path 124 subsequent to the first partially transmissive mirror 178 for captured radiation passing the first partially transmissive mirror 178. At the second partially transmissive mirror 180, the optical path 124 encloses an angle of incidence $\beta$ to the normal of the second partially transmissive mirror 180. In the third embodiment shown in FIG. 3, the angles of incidence, $\alpha$ and $\beta$, are essentially equal to 45°.

In an extended embodiment, one or all of the partially reflective mirrors 178, 180 are pivotable. One or two actuators are mechanically coupled to each of the pivotable partially transmissive mirrors 178 and 180. Each of the actuator is adapted to pivot the pivotable partially transmissive mirror between a first angular position and a second angular position. The controller 140 is adapted to control the one or more actuators. In the first angular position, the (first or second) pivotable partially transmissive mirror directs radiation captured on the optical path 124 into a first optical sub-branch, and vice versa. In the second angular position, the (first or second) pivotable partially transmissive mirror directs radiation captured on the optical path 124 into a second optical sub-branch, and vice versa. Different ophthalmic units or different ophthalmic sub-units are optically coupled to each of the optical sub-branches. Alternatively, the first sub-branch is coupled to a beam dump and the second sub-branch is coupled to one or more of the ophthalmic units 106, 108, 110, 112. In the first angular position, the captured radiation is directed to the first sub-branch coupled to the beam dump. The first angular position serves as a protective state for protecting the one or more of the ophthalmic units, e.g. in the case of high intensity of the captured radiation.

The optical branch coupler 104 according to the third embodiment thus provides a spectral splitting of captured radiation on the optical path 124 into a first optical branch 118 for radiation having a wavelength below 500 nm, into a second optical branch 120 for radiation having a wavelength in the spectral range from 500 nm to 750 nm, and into a third optical branch 122 for radiation having a wavelength above 750 nm.

The spectral splitting according to the wavelength-dependent first transmittance and $T_1$ and the second transmittance $T_2$ (described above for the third embodiment) are also realizable by the first embodiment or by the second embodiment, e.g., the optical interface 136 (shown in FIG. 1) can split captured radiation analogously to the transmittance and reflectance of the mirror 178.

Figure 4:
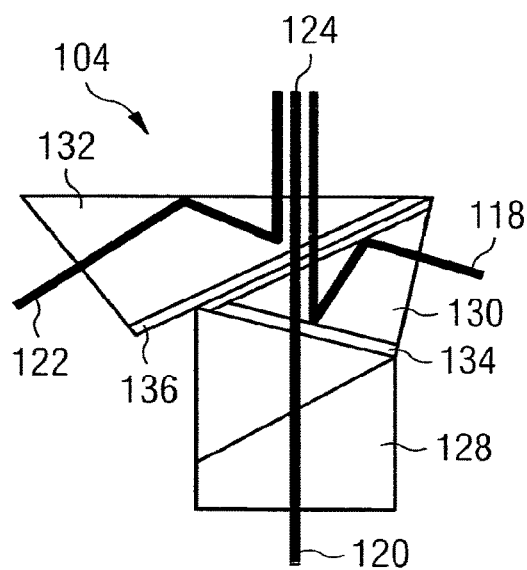
FIG. 4 schematically illustrates a cross section of an optical branch coupler comprised by each of the device embodiments of FIGS. 1 and 2.

FIG. 4 schematically illustrates further details of the optical branch coupler 104 applied in each of the first and the second embodiment. The optical branch coupler 104 comprises three glass prisms 128, 130 and 132. A first optical interface 134 between the glass prisms 128 and 130 comprises a first dichroic layer. A second optical interface 136 between the glass prisms 130 and 132 comprises a second dichroic layer. The second dichroic layer is transmissive in a first spectral range and a second spectral range. Captured radiation on the optical path 124 in a third spectral range is reflected from the second dichroic layer. The radiation components, for which spectral range the second dichroic layer is transmissive, enter the glass prisms 130. The first component is reflected from the first dichroic layer. The reflected first component defines the first optical branch 118. The second component passes through the first dichroic layer (such as the first optical interface 134). The second component thus defines the second optical branch 120. The third component reflected from the second dichroic layer (such as the second optical interface 136) defines the third optical branch 122.

Figure 5A:
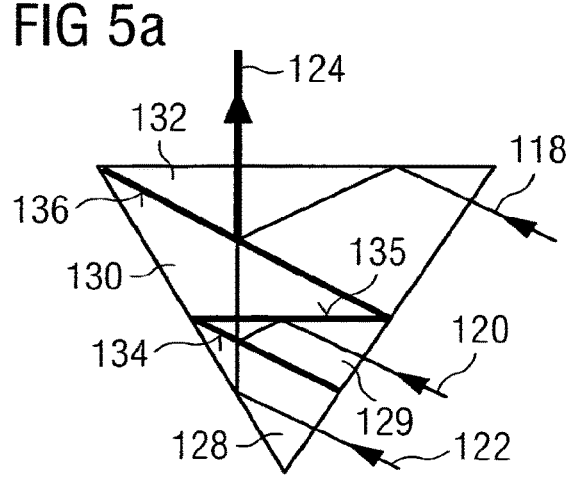
FIGS. 5a and 5b schematically illustrate composition and decomposition of radiation in an optical branch coupler, respectively.
Figure 5B:
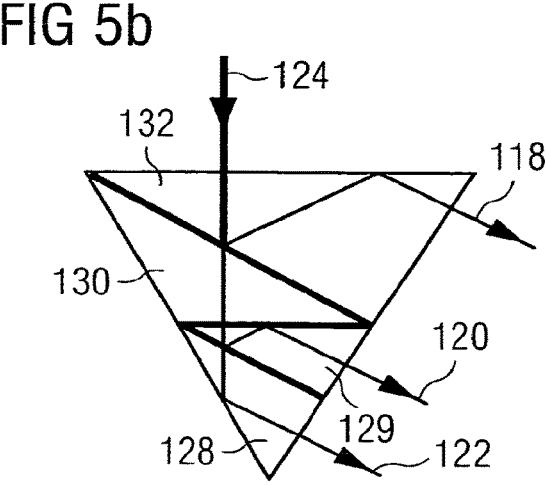

The FIGS. 5a and 5b schematically illustrate an alternative prism geometry of the optical branch coupler 104. The optical branch coupler 104 comprises four glass prisms 128, 129, 130 and 132. The optical interfaces 134, 135 and 136 include different dichroic layers. As shown in FIG. 5a, the different dichroic layers have different spectral transmittance and different spectral reflectance chosen so as to compose into the single optical path 124 output radiation in a first spectral range from the first optical branch 118, in a second spectral range from the second optical branch 120, and in a third spectral range from the third optical branch 122. FIG. 5b shows the corresponding decomposition of captured radiation from the single optical path 124 as a function of the spectral ranges into the three different optical branches 118, 120 and 122.

Figure 6A:
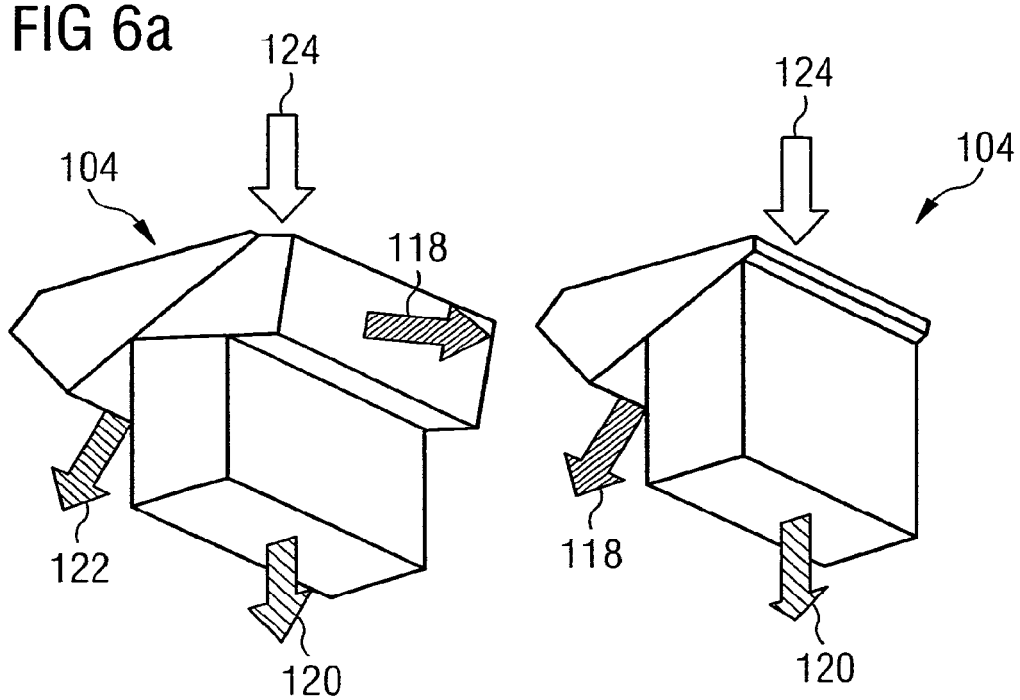
FIG. 6a is a schematic perspective view of two optical branch couplers adapted to couple three and two branches, respectively.
Figure 6B:
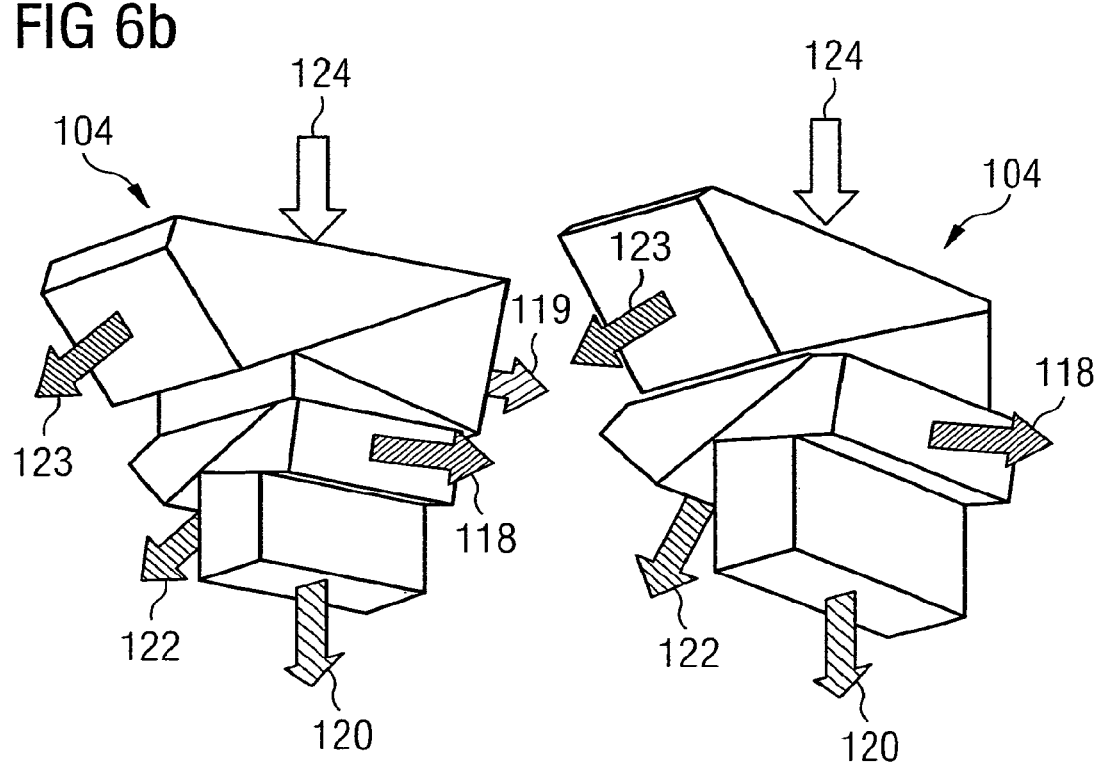
FIG. 6b is a schematic perspective view of two optical branch couplers adapted to couple five and four optical branches, respectively.

While above embodiments have been described for the case of three optical branches 118, 120 and 122, FIGS. 6a and 6b schematically show perspective views of optical branch couplers 104 for various numbers of optical branches. On the left half of FIG. 6a, a multibranched dichroic prism (as the optical branch coupler 104) is shown. The multibranched dichroic prism provides three optical branches 118, 120 and 122. The number of optical branches is also referred to as a number of "channels" of the dichroic prism. For a reduced embodiment of the device 100, a dichroic prism providing two optical branches 118 and 120 is used, as shown on the right half of FIG. 6a. FIG. 6b shows on the right half a multibranched dichroic prism (as optical branch couplers 104) providing four optical branches 118, 120, 122 and 123. A further a multibranched dichroic prism (as optical branch couplers 104) providing five optical branches 118, 119, 120, 122 and 123 is shown on the left half of FIG. 6b.

The optical lengths of the different optical branches in the optical couplers are different. Depending on the lengths or other linear dimensions of the glass prisms or dichroic crystal prisms, the optical lengths are predefined by the geometry and the index of refraction of the prisms. The index of refraction can depend on the polarisation of the radiation. The different optical lengths allow simultaneously detecting spatially separated anatomies, such as the anterior segment and the posterior segment of the eye 10 by the device 100. Furthermore, the prisms are in direct contact and glued together at the optical interfaces (such as the optical interfaces 134, 135 and 136). This allows for a compact and robust design of the device 100.

In addition, the device 100 can comprise a treatment unit as one of the ophthalmic units. The treatment unit is adapted to couple therapeutic radiation (as output radiation of the device 100) into one or more of the optical branches.

Particularly, the treatment unit can be a Laser-Assisted In-Situ Keratomileusis unit, or LASIK unit. The LASIK unit comprises a laser, e.g., an excimer laser adapted to generate output ultraviolet radiation for refractive surgery. More particularly, the treatment unit can be a femtosecond lenticle extraction unit, or FLEx unit. The FLEx unit comprises a laser, may be a femtosecond laser adapted to generate output in infrared or ultraviolet radiation. Furthermore the treatment unit can be used for keratoplasty or epithelium abrasion. As a further advantage, the other ophthalmic units can substantially simultaneously provide real time monitoring of the treatment. Alternatively or in addition, the treatment unit includes an Excimer laser or femtosecond laser.

As has become apparent, the device can integrate a plurality of different ophthalmic technologies (including diagnostics and/or treatment) in a more compact device. The device can complete a processing according to the different ophthalmic technologies faster. The ophthalmic technologies provided by the ophthalmic units can comprise any technology operating at a different wavelength of within a different spectral range.

The invention claimed is:
1. An ophthalmic system, comprising:
    a fixation target on a first optical path that is co-axial with an eye;
    an Optical Coherence Tomography (OCT) system in a first optical branch of the ophthalmic system on a second optical path, the OCT system adapted to perform an OCT measurement of an eye and output an OCT signal;
    a wavefront aberrometer in a second optical branch of the ophthalmic system on a third optical path, the wavefront aberrometer adapted to measure a wavefront of the eye and output a wavefront signal;
    a first partially transmissive mirror for coupling the third optical path with the second optical path;
    a digital camera in a third optical branch of the ophthalmic system on a forth optical path, the digital camera adapted to capture a digital image of the eye and output a digital image signal;
    an optical branch coupler comprising:
        a second partially transmissive mirror positioned on the first optical path and the second optical path and coupled with a first actuator for pivoting the second partially transmissive mirror between a first angular position and a second angular position; and
        a third partially transmissive mirror positioned on the first optical path and the third optical path and coupled with a second actuator for pivoting the third partially transmissive mirror between a third angular position and a fourth angular position,
        wherein a transmittance of the second partially transmissive mirror and a transmittance of the third partially transmissive mirror provides a spectral splitting of radiation in the first optical path between the optical branch coupler and the eye at a wavelength below 500 nm, in the first optical path between the optical branch coupler and the fixation target at a wavelength between 500 nm and 750 nm, and the second optical path at a wavelength above 750 nm; and
    a controller electrically coupled to the OCT system, wavefront aberrometer, and digital camera, the controller comprising a central processing unit (CPU) and a graphics engine adapted to:
        receive the OCT signal, the wavefront signal, and the digital image signal;
        generate a three-dimensional image of an anterior segment of the eye based on the received OCT signal;
        compute values for a sphere component, a cylinder component, and an axial component of the cylindrical component of a refractive power of the eye based on each of the received OCT signal, the received wavefront signal, and the received digital image signal; and
        output the three-dimensional image of the eye, together with the values for the sphere component, the cylinder component, and the axial component of the cylindrical component of the refractive power of the eye.

2. The ophthalmic system of claim 1, wherein:
    the OCT system is adapted to perform an OCT measurement of the eye and output an OCT signal during a surgical procedure;
    the wavefront aberrometer is adapted to measure the wavefront of the eye and output a real-time wavefront signal during the surgical procedure;
    the digital camera adapted to capture a digital image of the eye and output a real-time digital image signal during the surgical procedure; and
    the controller is adapted to compute values for the determined sphere component, cylinder component, and axial component of the cylindrical component based on the received real-time OCT signal and the received real-time wavefront signal.

3. The ophthalmic system of claim 1, wherein the controller is further adapted to determine one or more of a cornea thickness, a corneal curvature, an anterior chamber depth, a lens position, a lens thickness, a lens contour, a lens shape, an axial length, and a retina thickness of the eye, based on at least one of the received OCT signal and the received wavefront signal.

* * * * *